United States Patent
Li et al.

(10) Patent No.: US 9,762,217 B2
(45) Date of Patent: Sep. 12, 2017

(54) RANDOM SAMPLER ADAPTED TO ONE-DIMENSION SLOW-VARYING SIGNAL

(71) Applicant: INSTITUTE OF MICROELECTRONICS, CHINESE ACADEMY OF SCIENCES, Beijing (CN)

(72) Inventors: Dongmei Li, Beijing (CN); Qing Luo, Beijing (CN); Shengfa Liang, Beijing (CN); Hongzhang Yang, Beijing (CN); Xiaojing Li, Beijing (CN); Hao Zhang, Beijing (CN); Changqing Xie, Beijing (CN); Ming Liu, Beijing (CN)

(73) Assignee: INSTITUTE OF MICROELECTRONICS CHINESE ACADEMY OF SCIENCES, Beijing (CN)

( * ) Notice: Subject to any disclaimer, the term of this patent is extended or adjusted under 35 U.S.C. 154(b) by 28 days.

(21) Appl. No.: 14/888,335

(22) PCT Filed: Jul. 15, 2013

(86) PCT No.: PCT/CN2013/079363
§ 371 (c)(1),
(2) Date: Oct. 30, 2015

(87) PCT Pub. No.: WO2015/006898
PCT Pub. Date: Jan. 22, 2015

(65) Prior Publication Data
US 2016/0079969 A1    Mar. 17, 2016

(51) Int. Cl.
*H03K 4/08*    (2006.01)
*A61B 5/00*    (2006.01)
(Continued)

(52) U.S. Cl.
CPC ............ *H03K 4/08* (2013.01); *A61B 5/00* (2013.01); *H03K 3/84* (2013.01); *H03K 4/50* (2013.01)

(58) Field of Classification Search
CPC ... H03K 4/08; H03K 3/84; H03K 4/50; A61B 5/00
(Continued)

(56) References Cited

U.S. PATENT DOCUMENTS 8,301,674 B2 * 10/2012 Lee ................ G06F 7/588
708/250
9,536,661 B2 * 1/2017 Itoh ................ H01F 27/027

FOREIGN PATENT DOCUMENTS

CN    1489037 A    4/2004
CN    101510150 A    8/2009
(Continued)

*Primary Examiner* — Dinh T Le
(74) *Attorney, Agent, or Firm* — Christensen, Fonder, Dardi & Herbert, PLLC

(57) ABSTRACT

A sampler adapted to a one-dimension slow-varying signal, including: a signal preprocessing unit configured to preprocess an input signal; a slope-controllable sawtooth wave signal generating unit configured to generate a slope-controllable sawtooth wave signal and perform zero-resetting; a signal comparing unit configured to compare the preprocessed input signal from the signal preprocessing unit with the sawtooth wave signal and to output a pulse signal to the generating unit and a signal outputting unit when the preprocessed input signal is equal to the sawtooth wave signal; a counting unit configured to count a number of clock signals while the sawtooth wave signal generating unit is generating the sawtooth wave signal and to transmit the counted number to the signal outputting unit; the signal outputting unit configured to, upon receipt of the pulse signal output from the signal comparing unit, output the number counted by the counting unit at the moment.

6 Claims, 3 Drawing Sheets

(51) Int. Cl.
*H03K 3/84* (2006.01)
*H03K 4/50* (2006.01)

(58) Field of Classification Search
USPC ........................................ 327/9–94, 131–134
See application file for complete search history.

(56) References Cited

FOREIGN PATENT DOCUMENTS

| | | |
|---|---|---|
| CN | 101539847 A | 9/2009 |
| CN | 101968963 A | 2/2011 |
| JP | 2002-232406 A | 8/2002 |

\* cited by examiner

RANDOM SAMPLER ADAPTED TO ONE-DIMENSION SLOW-VARYING SIGNAL

CROSS-REFERENCE TO RELATED APPLICATION(S)

This application is a U.S. national phase application of PCT Application No. PCT/CN2013/079363 filed on Jul. 15, 2013, entitled "RANDOM SAMPLER FOR ONE-DIMENSIONAL SLOWLY-VARYING SIGNAL". This PCT Application is incorporated herein by reference in its entirety.

TECHNICAL FIELD

The disclosure generally relates to the technical field of signal collection, and more particularly, to a random sampler adapted to a one-dimension slow-varying signal.

BACKGROUND

Conventional signal sampling is typically performed periodically at a fixed frequency. According to the Nyquist sampling theorem, the minimum sampling rate is twice the bandwidth of a signal. Although such a sampling approach can ensure perfect restoration of the signal, hardware resources and storage space are wasted to some extent. In recent years, with the introduction of compressive sensing, the limitation imposed by the Nyquist sampling theorem has been broken. Exploration of sampling approaches which enable sampling at a rate lower than the Nyquist frequency has begun.

An existing sampler that samples at a rate lower than the Nyquist frequency is called analog to information converter (AIC), which employs a random sampler that performs frequency mixing using a pseudo random sequence. As illustrate in FIG. 1, the random sampler first performs frequency mixing of a sparse input signal with the pseudo random sequence, then samples the signal at a low frequency using a conventional integral sampler, which performs periodic sampling, and next transmits the sampled signal to a subsequent compressive sensing algorithm.

However, the analog to information converter merely mixes the input signal with a sequence consisting of +1 and −1, instead of realizing true random sampling. Meanwhile, its hardware complexity is relatively high, and a certain amount of storage space is needed. Further, for a one-dimension slow-varying signal, frequency mixing will increase the complexity of the signal. Therefore, the analog to information converter is not adapted to random sampling of the one-dimension slow-varying signal.

Accordingly, a random sampler which is more adapted to a one-dimension slow-varying signal is desired.

SUMMARY

Technical Problem to be Solved

To overcome the above-described drawbacks in the prior art, the present disclosure provides a random sampler adapted to a one-dimension slow-varying signal, in order to solve the high complexity problem with the random sampling circuit and to achieve the object of simplifying the circuit.

Technical Solution

To achieve the above object, the present disclosure provides a random sampler adapted to a one-dimension slow-varying signal. The random sampler comprises a signal preprocessing unit 1, a slope-controllable sawtooth wave signal generating unit 2, a signal comparing unit 3, a counting unit 4 and a signal outputting unit 5.

The signal preprocessing unit 1 is configured to preprocess an input signal and to transmit the preprocessed input signal to the signal comparing unit 3.

The slope-controllable sawtooth wave signal generating unit 2 is configured to generate a slope-controllable sawtooth wave signal, which is transmitted to the signal comparing unit 3, and to perform zero-resetting.

The signal comparing unit 3 is configured to compare the preprocessed input signal from the signal preprocessing unit 1 with the sawtooth wave signal generated by the slope-controllable sawtooth wave signal generating unit 2 and to output a pulse signal to the slope-controllable sawtooth wave signal generating unit 2 and the signal outputting unit 5 when the preprocessed input signal is equal to the sawtooth wave signal.

The counting unit 4 is configured to count a number of clock signals while the sawtooth wave signal generating unit 2 is generating the sawtooth wave signal and to send the counted number to the signal outputting unit 5.

The signal outputting unit 5 is configured to, upon receipt of the pulse signal output from the signal comparing unit 3, output the number counted by the counting unit 4 at the moment.

In the above solution, the preprocessing of the input signal by the signal preprocessing unit 1 comprises: reversing the input signal, so that more data can be collected in case of a sudden change of the signal so as to increase an average sampling rate of the random sampler.

In the above solution, the sawtooth wave signal generated by the slope-controllable sawtooth wave signal generating unit 2 is transmitted to the signal comparing unit 3, where the sawtooth wave signal is compared with the preprocessed input signal. When the sawtooth wave signal is equal to the preprocessed signal, the signal comparing unit 3 outputs the pulse signal to the slope-controllable sawtooth wave signal generating unit 2, which resets to zero and regenerates a new sawtooth wave signal.

In the above solution, the slope-controllable sawtooth wave generating unit 2 comprises a constant current source, a capacitor and a switch triggered by the pulse signal. A slope of the sawtooth wave signal is controlled by adjusting a current level of the constant current source. A voltage level of the sawtooth wave signal is reset to zero by the switch triggered by the pulse signal.

In the above solution, the signal comparing unit 3 is constituted of a comparer. The sawtooth wave signal generated by the slope-controllable sawtooth wave signal generating unit 2 and the input signal preprocessed by the signal preprocessing unit 1 are input to a positive input terminal and a negative input terminal of the comparer, respectively. When the sawtooth wave signal is lower than the input signal, an output terminal of the comparer is at a low level. When the sawtooth wave signal is equal to or higher than the input signal, the output terminal of the comparer is at a high level and outputs a pulse signal to the slope-controllable sawtooth generating unit 2, which resets to zero and regenerates a new sawtooth wave signal, and the signal outputting unit 5, which outputs the number counted at the moment.

In the above solution, the counting unit 4 is implemented using a counter, and the number counted by the counter conveys time information and information about a voltage level of the sawtooth wave signal which are used for data restoration at a computer connected to an output terminal of the signal outputting unit 5.

In the above solution, an incentive signal for the signal outputting unit 5 is the pulse signal generated by the signal comparing unit 3, and an output of the signal outputting unit 5 is an instantaneous number generated by the counting unit 4.

Advantage

The above technical solutions according to the present disclosure have the following advantages.

1. As can be seen from the structure of the random sampler according to the present disclosure, no storage unit, AD sampler or compressing unit required for the conventional sampling approach is needed. Thus, due to the omission of data storage, hardware cost and power consumption can be saved and hardware complexity is low. In addition, true random sampling can be realized. Therefore, the random sampler according to the present disclosure is more adapted to sampling a one-dimension slow-varying signal.

2. By applying the principle of compressive sensing to reduce sampling frequency, the random sampler according to the present disclosure allows the original signal to be reconstructed using a sampling rate lower than the Nyquist frequency. By way of example, supposing ten data points need to be sampled per second for a signal according to the Nyquist frequency, the sampling rate can be reduced to two to three data points per second if the random sampler according to the present invention is used for sampling. Because sampling points are determined jointly by the sawtooth wave signal and the input signal according to the disclosure and one sampling point is recorded each time these two signals equals to each other, that is, the sampling frequency can be reduced by reducing the slope of the sawtooth wave signal. Only if requirements for compressive sensing which serves as the theoretical basis are satisfied in the case of low sampling rate, the signal can be reconstructed using a compressive sensing reconstruction algorithm.

3. The random sampler according to the present disclosure has a lower hardware complexity than the conventional approach and AIC sampler and is easier to implement. Thus, hardware cost and power consumption of the system can be reduced.

4. Without requiring frequency mixing which would increases the complexity of the signal, the random sampler according to the present disclosure is more adapted to sampling a one-dimension slow-varying signal, as the complexity of the signal would not be increased.

5. As compared with an AIC system where in order to determine the measurement matrix it is necessary to know all values of the pseudo random sequence and then determine which part of the sequence is taken, the random sampler according to the present disclosure allows the measurement matrix to be obtained as long as the value of the counter is received. Thus, it is easier to determine the measurement matrix. Accordingly, it is easier to perform reconstruction based on the collected signal by applying the compressive sensing approach.

6. The output of the random sampler according to the present disclosure is the number generated by the counter and does not need to be stored before being transmitted. Therefore, storage space can be saved.

BRIEF DESCRIPTION OF THE DRAWINGS

For further illustrating the present disclosure, detailed description will be given below in conjunction with embodiments and accompany drawings, in which.

DETAILED DESCRIPTION OF EMBODIMENTS

In order for the objects, solutions and advantages of the present disclosure to be more clear and apparent, detailed description will be given in the following in conjunction with detailed embodiments and with reference to accompanying drawings.

Figure 1:
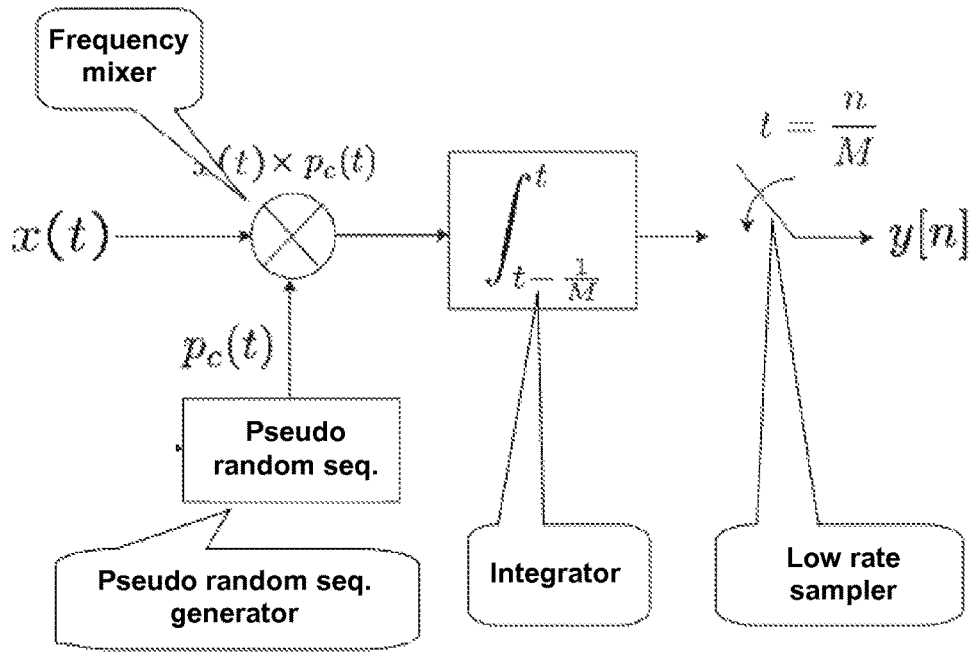
FIG. 1 is a diagram illustrating a structure of a random sampler in the prior art.

The random sampler according to the present disclosure is completely different in principle from the AIC sampler shown in FIG. 1. The AIC sampler shown in FIG. 1 enables random sampling of a signal by performing frequency mixing for the signal and then performing low-rate sampling, while the random sampler according to the present disclosure enables random sampling of a signal by making use of randomness of intersections between two compared signals. As no frequency mixing is performed for the signal, the complexity of the signal is not increased. The above-described difference in principle leads to completely different hardware implementations.

Figure 2:
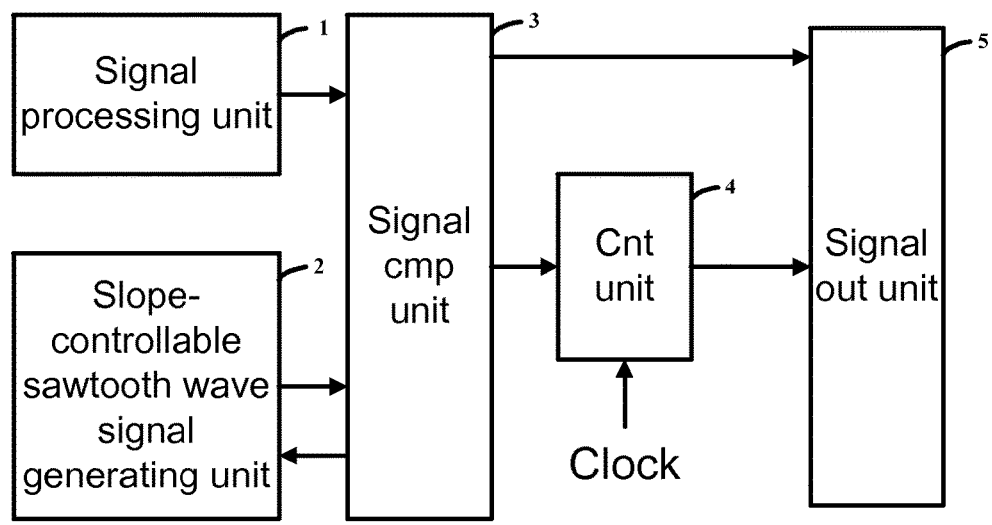
FIG. 2 is a diagram illustrating a structure of a random sampler adapted to a one-dimension slow-varying signal according to an embodiment of the disclosure.

FIG. 2 is a diagram illustrating a structure of a random sampler adapted to a one-dimension slow-varying signal according to an embodiment of the disclosure. As illustrated, the random sampler comprises a signal preprocessing unit 1, a slope-controllable sawtooth wave signal generating unit 2, a signal comparing unit 3, a counting unit 4 and a signal outputting unit 5. A pulse signal output from the signal comparing unit 3 controls the slope-controllable sawtooth wave signal generating unit 2 and the signal outputting unit 5. In the following, these units will be explained in detail.

1. Signal Preprocessing Unit

Figure 3:
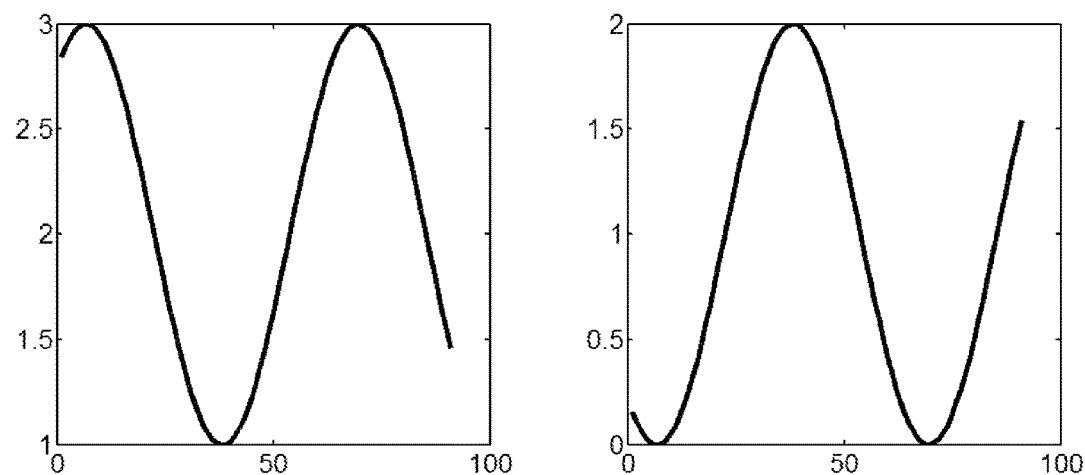
FIG. 3 is a diagram illustrating an effect to be achieved by a signal preprocessing unit in FIG. 2.

The signal preprocessing unit 1 is configured to preprocess an input signal before it arrives at the signal comparing unit 3 and to transmit the preprocessed signal to the signal comparing unit 3, so that more data can be collected in case of a sudden change of the signal so as to increase an average sampling rate. The preprocessing means to reverse the input signal. Considering that the random sampler is characterized by sampling data closer to zero at a high sampling frequency, the signal is preprocessed to be reversed, so that it can be sampled better as its level increases. Because the data sampling frequency of the random sampler according to the present disclosure increases as the signal gets closer to zero while the sudden change of a sensed signal typically occurs in a positive direction, preprocessing that mainly comprises reversing the input signal needs to be performed for the collected data, in order to meet the practical requirement of collecting more data in case of a change. The effect intended to be achieved by the preprocessing is shown in FIG. 3. As illustrated, the signal on the right side is a reversal of the signal on the left side.

2. Slope-Controllable Sawtooth Wave Signal Generating Unit

The slope-controllable sawtooth wave signal generating unit 2 is configured to generate a slope-controllable sawtooth wave signal and to perform zero-resetting. The sawtooth wave signal is transmitted to a signal comparing unit 3 where it is compared with the preprocessed input signal. When these two signals are equal to each other, the slope-controllable sawtooth wave signal generating unit 2 resets to zero and regenerates a new sawtooth wave signal. The above actions are repeated, so that the sawtooth wave signal generated by the random sampler according to the disclosure is compared with the input signal, the randomness of their equality is made use of to generate a random pulse, and then the subsequent counter and signal outputting unit are used to transmit characteristic information of points that are equal to a computer, where restoration is performed using a compressive sensing reconstruction algorithm. Compressive sensing is in essence solving an underdetermined equation $y_i=\langle \phi,x \rangle$. $y_i$ on the left side of the underdetermined equation $y_i=\langle \phi,x \rangle$ denotes M samples obtained by the compressive sensing and is a matrix consisting of sampled signals. On the right side of the equation is a product of an original signal x and a coefficient matrix $\phi$, which is for sparsifying and measuring the original signal. The signal output from the counter obtained according to the disclosure contains information on the measurement matrix and information on measured values, and the sparse matrix can be customized. Accordingly, the fundamental underdetermined equation for the compressive sensing has been constructed. In prior art, mature algorithms for solving the underdetermined equation already exist and can be used straightforwardly. For more details, reference can be made to common signal reconstruction algorithms described below. In addition, the sawtooth wave signal and the input signal are continuously compared, and sampling is performed once when the signals are equal to each other. The smaller the slope of the sawtooth wave signal is, the later the time when the signals meet with each other is. Therefore, the slope of the sawtooth wave signal dictates the average sampling rate of the random sampling. In order to adapt to different signals, it shall be ensured that the slope of the sawtooth wave signal is adjustable.

Figure 4:
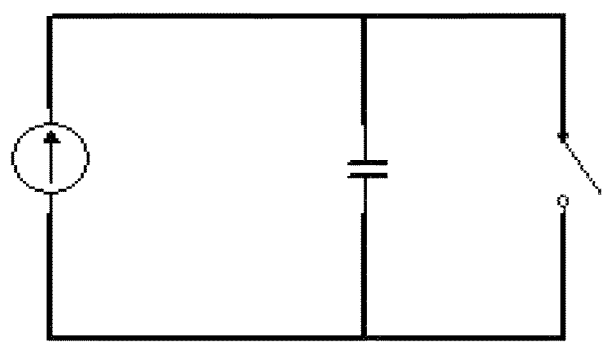
FIG. 4 is a diagram illustrating a structure of a slope-controllable sawtooth wave signal generating unit in FIG. 2.

FIG. 4 is a diagram illustrating a structure of the slope-controllable sawtooth wave signal generating unit, which comprises a constant current source, a capacitor and a switch triggered by the pulse signal. The slope of the sawtooth wave signal is controlled by adjusting a current level of the constant current source, and the level of the sawtooth wave signal is cleared to zero by the switch triggered by the pulse signal.

Here, the compressive sensing reconstruction algorithm will be introduced briefly. Compressive sensing is a novel information acquisition theory and is a signal collecting and reconstructing method based on sparse representation of signal, uncorrelation of measurement matrix and approximation theory. As that theory suggests, as long as a signal is sparse or is compressed according to a basis temporally, structural information of the signal can be obtained at a sampling rate much lower than that required by the Nyquist sampling theorem, and the signal can be accurately reconstructed by using a reconstruction algorithm. The compressive sensing only includes two stages: projecting the signal onto observation vectors to obtain observed values; and reconstructing the signal from the observed values by using the reconstruction algorithm.

Let us suppose x is a signal having a length of N and a sparsity of K(K<N). The sparsity K indicates that x itself has K non-zero elements or its expansion coefficients in a certain transform domain $\Psi$ include K non-zero elements. Projections of signal x (supposing the signal corresponds to K coefficients in the transform domain $\Psi$) on observation vectors may be expressed as:

$$y_i=\langle \phi_i,x \rangle$$

where $y_i$ denotes M samples obtained by the compressing sensing, i=1, . . . M, M<N, and $(\phi_i)_{i=1}^M$ denotes the set of observation vectors. The observation basis consisting of $(\phi_i)_{i=1}^M$ is uncorrelated to the transform basis $\Psi$.

The key to signal reconstruction is to find a sparse representation of signal x in domain $\Psi$. The solution having a coefficient structure may be found by solving a $l_0$ norm optimization problem:

$$\min\|\Psi_x^T\|_0 s.t.\ y=\Phi x.$$

Because the optimization problem expressed as the above equation is an NP-hard problem which is difficult to solve, $l_0$ constraint may be replaced with $l_1$ constraint:

$$\min\|\Psi_x^T\|_1 s.t.\ y=\Phi x.$$

Then, the samples obtained by the compressive sensing retain the structure and related information of the original signal. Therefore, without having to reconstruct the signal, the signal detection task can be completed by directly extracting characteristic values from the samples by using a detection algorithm and making judgment.

Common signal reconstruction algorithms include minimum $l_0$ norm model, matching pursuit algorithm and orthogonal matching pursuit algorithm.

1) Minimum $l_0$ Norm Model

Mathematically, a compressive sensing based signal reconstruction problem is a problem of finding out the simplest solution of an equation set (for which the number of equations is less than the number of unknown values to be determined). $l_0$ norm characterizes the number of non-zero elements in the signal, thereby enabling the result to be as sparse as possible. Typically, we use the following equation to describe the minimum $l_0$ norm optimization problem:

$$\min\|X\|_0 s.t.\ Y=\Phi X \quad (3.1)$$

In practice, a certain degree of error is allowed. Thus, the original optimization problem is converted into a simpler approximation, where $\delta$ is an infinitesimal constant:

$$\min\|X\|_0 s.t.\|Y-\Phi X\|_2^2 \le \delta \quad (3.2)$$

However, such a problem is very difficult to solve, because its numerical solution deriving calculation is very instable.

Reconstruction algorithms of the matching pursuit type solve the minimum $l_0$ norm problem. The earliest proposed are matching pursuit (MP) algorithm and orthogonal matching pursuit (OMP) algorithm.

2) Matching Pursuit Algorithm

The basic idea of the matching pursuit algorithm is to, in each iteration, make a sparse approximation by selecting from an overcomplete atom base (i.e., a sensing matrix) an atom that best matches a signal and calculate a residual for which a best matching atom is selected subsequently. After several iterations, the signal can be linearly represented by some atoms. However, due to the non-orthogonality among projections the signal to the set of the selected atoms (i.e., column vectors in the sensing matrix), the result of each iteration may be suboptimal. Therefore, in order to achieve a desired convergence result, many iterations are needed typically.

Typically, algorithms of the matching pursuit type calculate a correlation coefficient u by determining an absolute value of an inner product of the residual r and the atoms in the sensing matrix $\Phi$:

$$u=\{u_j | u_j=|\langle r, \phi_j \rangle|, j=1,2,\ldots,N\},$$

and approximating the signal and updating the residual by using the least square method:

$$\hat{X} = \arg\min_{i \in R^\wedge} \|Y - \Phi_\wedge X\|$$

$$r_{new} = Y - \Phi_\wedge \hat{X}.$$

3) Orthogonal Matching Pursuit Algorithm

The orthogonal matching pursuit algorithm (OMP) is one of the earliest greedy iterative algorithms. The algorithm continues to use the atom selection criterion in the matching pursuit algorithm, except that optimal iterations are ensured by orthogonalizing the set of the selected atoms through recursion and thus the number of iterations is reduced. The OMP algorithm effectively overcomes the problem with the matching pursuit algorithm—many iterations are typically needed in order to achieve a desired convergence result.

The OMP algorithm orthogonalizes the selected atoms by using the Gram-Schmidt orthogonalization procedure, and then projects the signal on the space constituted by these orthogonalized atoms to obtain components and residuals of the signal on the selected atoms, and next decompose the residuals in the same manner. At each decomposition step, the selected atoms satisfy a certain condition. Therefore, the residuals diminish quickly as the decomposition process proceeds. Orthogonalizing the set of the selected atoms through recursion optimal iterations ensures optimal iterations, thereby reducing the number of the number of iterations.

An OMP reconstruction algorithm is subject to a given number of iterations. Such an algorithm which forcibly terminates the iterative process requires OMP to perform quite a lot of linear measurements for ensuring an accurate reconstruction. In short, it selects columns of $\Phi$ by using a greedy iterative algorithm so that the column selected in each iteration is correlated to the current redundant vector to the maximum extent, subtracts related part from the measurement vector and iterates until the number of iterations reaches a sparsity K. Then, iterating is forcibly stopped.

Detailed steps of the OMP algorithm are as follows:

(1) initializing a residual $r_0=Y$, a number of iterations n=1, and index sets $\Lambda=\emptyset$ and $J=\emptyset$;

(2) calculating a correlation coefficient u, and storing an index corresponding to the maximum value in u into J;

(3) updating a support set $\Phi_\Lambda$, wherein $\Lambda=\Lambda \cup J_0$;

(4) applying equation (3.3) to obtain $\hat{X}$, and meanwhile updating the residual by applying equation (3.4);

(5) if $\|r_{new}-r\| \geq \epsilon_2$, then setting $r=r_{new}$ and n=n+1 and returning to step (2); otherwise, stopping iterating.

3. Signal Comparing Unit

The signal comparing unit 3 is configured to compare the input signal from the signal preprocessing unit 1 and the sawtooth wave signal generated by the slope-controllable sawtooth wave signal generating unit 2 and to output a pulse signal to the slope-controllable sawtooth wave signal generating unit 2 and the signal outputting unit 5 when these two signals are equal, for resetting of the slope-controllable sawtooth wave signal generating unit 2 and functioning of the signal outputting unit 5. Among the units of the random sampler according to the present disclosure, the signal comparing unit 3 is the easiest to implement in hardware, although it is the very core of the random sampler. Mainly by comparing the sawtooth wave signal generated by the slope-controllable sawtooth wave signal generating unit 2 with the input signal, a random pulse signal is generated, thereby enabling random sampling to be truly realized.

The signal comparing unit 3 is mainly constituted of a comparer. The sawtooth wave signal generated by the slope-controllable sawtooth wave signal generating unit 2 and the input signal preprocessed by the signal preprocessing unit 1 are input to a positive input terminal and a negative input terminal of the comparer, respectively. When the sawtooth wave signal is lower than the input signal, an output terminal of the comparer is at a low level. When the sawtooth wave signal is equal to or higher than the input signal, the output terminal of the comparer is at a high level, and the slope-controllable sawtooth wave generating unit 2 resets and regenerates a new sawtooth wave signal. Meanwhile, the signal output unit 5 outputs the number counted at the moment to the computer.

4. Counting Unit

The counting unit 4 is configured to count a number of clock signals while the sawtooth wave signal generating unit 2 is generating the sawtooth wave signal and to transmit the countered number to the signal outputting unit 5. The counting unit 4 is typically implemented using a counter. As the slope of the sawtooth wave signal is known, the number counted by the counter conveys time information and information about a voltage level of the sawtooth wave signal which are used for data restoration at the computer. Here, the occurrence frequency of the clock signals is adjustable, in order to ensure restoration of the desired signal.

5. Signal Outputting Unit

The signal outputting unit 5 is configured to, upon receipt of the pulse signal output from the signal comparing unit 3, output the number counted by the counting unit 4 at the moment. An incentive signal for the signal outputting unit 5 is the pulse signal generated by the signal comparing unit 3, and an output of the signal outputting unit 5 is an instantaneous number generated by the counting unit 4.

Figure 5:
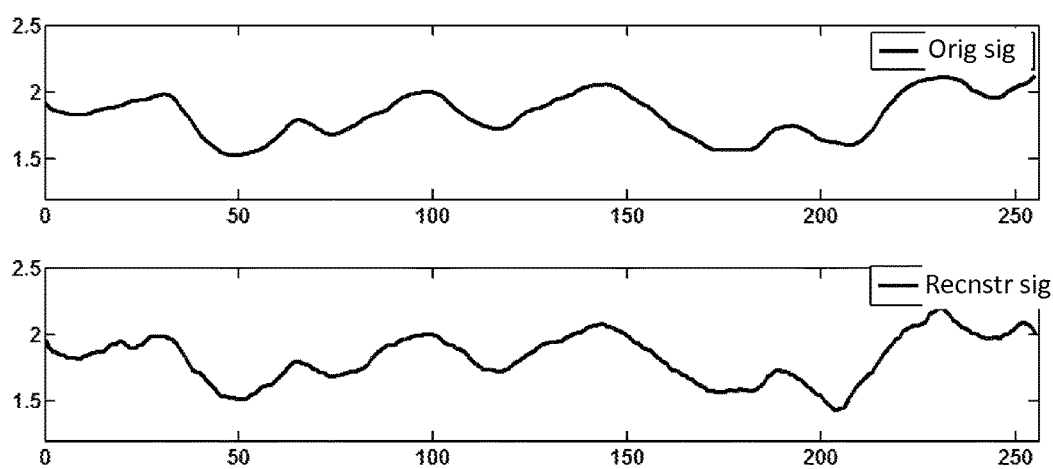
FIG. 5 is a diagram illustrating a comparison and an error between a signal, which is restored from data randomly sampled by the random sampler according to the present disclosure by using a compressive sensing based OMP algorithm, and an original signal.

From a simulated case where a signal from a gas sensor is sampled and restored by using a random sampling method and the random sampler adapted to a one-dimension slow-varying signal according to the disclosure, it can be found that the random sampling method is practicable in an allowable degree of error, as shown in FIG. 5 which illustrates a comparison between the original signal and the signal restored from the random samples.

As can be seen from the above embodiments, in principle, the random sampler according to the disclosure actually realizes random sampling of a signal in the time domain. Meanwhile, real randomness is achieved, because the AIC sampler shown in FIG. 1 performs frequency mixing using a pseudo random sequence instead of performing real random frequency mixing. From the circuit structure perspective, the hardware circuit of the random sampler according to the disclosure does not include a storage, a pseudo random sequence generator or an ADC chip. Thus, the circuit is simpler and is easy to implement, and storage space and power consumption are saved.

The above detailed embodiments further describe the object, technical solutions and advantages of the disclosure. It shall be appreciated that the above contents are just detailed embodiments of the disclosure but are not intended to limit the disclosure. Any alterations, equivalent replacements, improvements, etc. made within the spirit and scope of the disclosure are intended to fall within the protection scope of the disclosure.

What is claimed is:

1. A random sampler adapted to a one-dimension slow-varying signal, comprising: a signal preprocessing unit, a slope-controllable sawtooth wave signal generating unit, a signal comparing unit, a counting unit and a signal outputting unit, wherein
the signal preprocessing unit is configured to preprocess an input signal and to transmit the preprocessed input signal to the signal comparing unit,
the slope-controllable sawtooth wave signal generating unit is configured to generate a slope-controllable sawtooth wave signal, which is transmitted to the signal comparing unit, and to perform zero-resetting,
the signal comparing unit is configured to compare the preprocessed input signal from the signal preprocessing unit with the sawtooth wave signal generated by the slope-controllable sawtooth wave signal generating unit and to output a pulse signal to the slope-controllable sawtooth wave signal generating unit and the signal outputting unit when the preprocessed input signal is equal to the sawtooth wave signal,
the counting unit is connected to the slope-controlled sawtooth wave signal generating unit via the signal comparing unit and configured to count a number of clock signals while the sawtooth wave signal generating unit is generating the sawtooth wave signal and to transmit the counted number to the signal outputting unit, and
the signal outputting unit is configured to, upon receipt of the pulse signal output from the signal comparing unit, output an instantaneous counted number received from the counting unit.

2. The random sampler according to claim 1, wherein the preprocessing of the input signal by the signal preprocessing unit comprises: reversing the input signal.

3. The random sampler according to claim 1, wherein
the sawtooth wave signal generated by the slope-controllable sawtooth wave signal generating unit is transmitted to the signal comparing unit, where the sawtooth wave signal is compared with the preprocessed input signal, and
when the sawtooth wave signal is equal to the preprocessed signal, the signal comparing unit outputs the pulse signal to the slope-controllable sawtooth wave signal generating unit, which resets to zero and regenerates a new sawtooth wave signal.

4. The random sampler according to claim 3, wherein
the slope-controllable sawtooth wave generating unit comprises a constant current source, a capacitor and a switch triggered by the pulse signal, wherein a slope of the sawtooth wave signal is controlled by adjusting a current level of the constant current source and a voltage level of the sawtooth wave signal is reset to zero by the switch triggered by the pulse signal.

5. The random sampler according to claim 1, wherein
the signal comparing unit is constituted of a comparer,
the sawtooth wave signal generated by the slope-controllable sawtooth wave signal generating unit and the input signal preprocessed by the signal preprocessing unit are input to a positive input terminal and a negative input terminal of the comparer, respectively,
when the sawtooth wave signal is lower than the input signal, an output terminal of the comparer is at a low level,
when the sawtooth wave signal is equal to or higher than the input signal, the output terminal of the comparer is at a high level and outputs a pulse signal to the slope-controllable sawtooth generating unit and the signal outputting unit, so that the slope controllable sawtooth generating unit resets to zero to regenerate a new sawtooth wave signal, and the signal outputting unit outputs the instantaneous counted number.

6. The random sampler according to claim 1, wherein
the counting unit is implemented using a counter, and the number counted by the counter conveys time information and information about a voltage level of the sawtooth wave signal which are used for data restoration at a computer connected to an output terminal of the signal outputting unit.

* * * * *